US007025998B2

(12) United States Patent
Senin et al.

(10) Patent No.: US 7,025,998 B2
(45) Date of Patent: Apr. 11, 2006

(54) PHYTOESTROGENS AND PROBIOTIC FOR WOMEN'S HEALTH

(75) Inventors: Paolo Senin, Monza (IT); Ivo Setnikar, Milan (IT); Angelo Luigi Rovati, Monza (IT)

(73) Assignee: Rotta Research Laboratorium S.p.A., Milan (IT)

( * ) Notice: Subject to any disclaimer, the term of this patent is extended or adjusted under 35 U.S.C. 154(b) by 0 days.

(21) Appl. No.: 10/448,405

(22) Filed: May 30, 2003

(65) Prior Publication Data

US 2004/0241260 A1 Dec. 2, 2004

(51) Int. Cl.
*A61K 35/78* (2006.01)
*A61K 31/35* (2006.01)
*A01N 63/00* (2006.01)

(52) U.S. Cl. .................. 424/757; 424/93.1; 424/93.45; 514/456

(58) Field of Classification Search ................ 424/757, 424/93.1, 93.45; 514/456
See application file for complete search history.

(56) References Cited

U.S. PATENT DOCUMENTS

| | | | | |
|---|---|---|---|---|
| 4,110,477 | A * | 8/1978 | Naruse et al. | 426/46 |
| 4,220,660 | A | 9/1980 | Brock | |
| 5,498,631 | A | 3/1996 | Gorbach et al. | |
| 5,516,528 | A | 5/1996 | Hughes et al. | |
| 5,702,752 | A | 12/1997 | Gugger et al. | |
| 5,792,503 | A | 8/1998 | Gugger et al. | |
| 5,830,887 | A | 11/1998 | Kelly | |
| 6,033,714 | A | 3/2000 | Gugger et al. | |
| 6,150,399 | A | 11/2000 | Patel et al. | |
| 6,171,638 | B1 | 1/2001 | Gugger et al. | |
| 6,261,565 | B1 | 7/2001 | Empie et al. | |
| 6,294,166 | B1 | 9/2001 | Hsia | |
| 6,344,217 | B1 * | 2/2002 | Ruepp | 424/581 |
| 6,375,994 | B1 * | 4/2002 | Paul et al. | 424/757 |
| 6,391,309 | B1 | 5/2002 | Empie et al. | |
| 6,447,809 | B1 * | 9/2002 | Krumhar et al. | 424/602 |
| 6,497,906 | B1 | 12/2002 | Kelly | |
| 6,716,424 | B1 * | 4/2004 | Shimizu et al. | 424/93.44 |
| 2002/0114786 | A1 * | 8/2002 | Fabre et al. | 424/93.3 |
| 2002/0182274 | A1 | 12/2002 | Lu | |
| 2003/0008023 | A1 | 1/2003 | Lu | |
| 2003/0031726 | A1 * | 2/2003 | Hendricks | 424/602 |

FOREIGN PATENT DOCUMENTS

| | | | |
|---|---|---|---|
| EP | 0 002 495 B1 | | 2/1984 |
| EP | 1025850 | * | 8/2000 |
| EP | 1 186 295 A | | 3/2002 |
| EP | 1186295 | * | 3/2002 |
| JP | 09238647 | * | 9/1997 |
| JP | 2001 333692 A | | 12/2001 |
| JP | 2001333692 | * | 12/2001 |
| JP | 2001340059 | * | 12/2001 |

OTHER PUBLICATIONS

"Body Measurements, Bone Mass, and Fractures" by Suzanne C. Ho, Clinical Orthopaedics and Related Research, No. 323m pp. 75-80, 1996.

"Isoflavone-Rich soy protein isolate attenuates bone loss in the lumbar spine of perimenopausal women", by D. Lee Alekel, et al., American Journal Clinical Nutrition, pp. 844-852, 679-680, 2000.

"Hight Dietary Phytoestrogen Intake is Associated with Higher Bone Mineral Density in Postmenopausal but Not Premenopausal Women", by Jie Mei et al., The Journal of Clinical Endocrinology & Metabolism, pp. 5217-5221, 2001.

"Soy Protein and Isoflavones: their effects on blood lipids and bone density in postmenopausal women", by Susan M. Potterm, et al., American Journal Clinical Nutrition., pp. 1375S-1379S, 1998.

"Dietary Inclusion of Whole Soy Foods Results in Significant Reductions in Clinical Risk Factors for Osteoporosis and Cardiovascular Disease in Normal Postmenopausal Women", by Michael D. Scheiber et al., the Journal of the North American Menopause Society, pp. 384-392, 2001.

"Phyloestrogens Reduce Bone Loss and Bone Resorption in Pophorectomized Rats", by Christine Draper et al., American Society for Nutritional Sciences, pp. 1795-1999, Nov. 20, 1996.

"Soy Isoflavone Aglycones are Absorbed Faster and in Higher Amounts than Their Glucosides in Humans", by Toru Izumi et al., American Society for Nutritional Sciences, pp. 1695-1699, Oct. 1999.

"Production and Metabolism of Lignans by the Human Faccal Flora", S.P. Borriello et al., journal of Applied Bacteriology, pp. 37-43, 1985.

"Nosteroidal Estrogens of Dietary Origin: Possible Roles in Hormone-Dependent Disease", KDR Setchell, et al., The American Journal of Clinical Nutrition, pp. 569-578, Sep. 1984.

Japanese Abstract, Sec. Ch, Week 200229, Derwent Pub. Ltd., London, GB;, AN 2002-231337, XP002293149 (2001).

P. De Boever, R. Wouters and W. Verstaete: "Combined use of Lactobacillus reuteri and soygerm powder as food supplement" Letters in Applied Microbiology, vol. 33, No. 6, Dec. 2001, pp. 420-424, XP002293148 p. 420, right-hand col., lines 14-24, p. 423, right-hand col., line 29-p. 424, left-hand col., line 14.

* cited by examiner

*Primary Examiner*—Christopher R. Tate
(74) *Attorney, Agent, or Firm*—Sughrue Mion, PLLC

(57) ABSTRACT

A composition for the relief and/or prevention of climacteric and menopausal disorders affecting women in pre-, peri- or post-menopause, comprising Soy Isoflavones and viable lactic acid bacteria preferably *Lactobacillus* sporogenes aimed to enhance the absorption of Soy Isoflavones, the composition being provided in dosage forms for oral administration. Preferably the composition also comprises *Equisetum arvense* dry extract and a pharmaceutically acceptable calcium salt and/or Vitamin $D_3$.

16 Claims, No Drawings

PHYTOESTROGENS AND PROBIOTIC FOR WOMEN'S HEALTH

TECHNICAL FIELD

The present invention relates to new compositions to be orally administered as tablets, capsules or powder for extemporaneous suspension, intended to enhance bone health and general well-being in climacteric and menopausal women.

BACKGROUND OF THE INVENTION

Postmenopausal osteoporosis due to the ovarian hormone deficiency is the most common cause of bone loss in women. The disorder is prevented by the administration of exogenous estrogen hormones, i.e. by an appropriate Hormone Replacement Therapy (HRT). The synthetic estrogen hormones used for this purpose are potent drugs and, if not properly used, may be associated with side effects, especially by long term administration.

The incidence of fractures ascribable to osteoporosis is lower in Asia than in Western countries. This difference has been attributed to the extensive use of soy-based foods [1] and in particular to some isoflavones that are present in soybeans. In fact, the efficacy of the soy isoflavones (SIs) on the trophism of the bones in post-menopause was demonstrated in several clinical studies [2, 3, 4, 5] and is supported by studies in ovariectomized rats [6].

Soybeans contain mainly two isoflavones, genistin and daidzin. Genistin (MW 432.22) is the β-glucoside of genistein (MW 270.24). Daidzin (MW 416.23) is the β-glucoside of daidzein (MW 254.24). Genistin and daidzin are relatively large molecules; they are very water-soluble and highly polar. These properties hinder their absorption from the gastrointestinal tract and therefore the bioavailability of the estrogen moiety.

To be absorbed and rendered bioavailable, the SIs must be hydrolyzed to aglycons, i.e. separated from the glucoside component [7]. This takes place by the action of special enzymes, the glycosidases. However, the human gastrointestinal tract and that of many mammalians does not secrete glycosidases and therefore the isoflavones cannot be hydrolyzed to become bioavailable. Conversely, some micro-organisms of the intestinal flora and in particular some lactic acid bacteria, produce the glycosidases required for the mentioned hydrolytic process that is necessary for the absorption of the SIs [8, 9]. The presence of glycosidase-producing bacteria in the gastrointestinal tract is therefore the prerequisite for the absorption and the efficacy of the SIs.

The intestinal flora varies greatly between individuals and, even in the same subject, it varies in function of the diet, climate, drug therapies, diseases, etc. Thus, in many subjects, the glycosidase production by the intestinal flora can be scarce or even absent, jeopardizing the absorption of the SIs.

Object of the present invention is to provide a composition for oral administration, particularly as a dietary supplement, for the mitigation, relief, and/or prevention of climacteric and postmenopausal disorders affecting women in pre-, peri- and post-menopause, including dismetabolism of bones that causes bone loss and structural changes with an increases of fracture risk.

SUMMARY OF THE INVENTION

The present invention provides a composition for the relief and prevention of climacteric and postmenopausal disorders comprising an effective amount of Soy Isoflavones and viable lactic acid bacteria, the composition being provided in dosage forms for oral administration.

The composition includes soy isoflavones with estrogenic activity and lactic acid bacteria to produce glycosidases in the intestine, aimed to split the ingested isoflavone glucosides into the aglycons that can be absorbed and to insure in all subjects the bioavailability of the administered SIs.

The invention also provides a method for the relief and prevention of climacteric and menopausal disorders, comprising the oral administration of an effective amount of the above mentioned composition to an individual in need thereof.

In principle, any type of lactic acid bacteria is suitable for the composition of the invention. In fact, lactic acid bacteria are probiotics that provide several benefits, because:

- They produce lactic acid that acidifies the intestinal content creating adverse condition for the growth of several pathogenic micro-organisms (*Coli, Candida*, etc.) and, conversely, creating favourable conditions for the absorption of calcium, of iron, of phosphorus and of other nutrients.
- By these mechanisms, and through the lowering of pH resulting from the production of lactic acid, the lactic acid bacteria improve and balance the intestinal flora. This is very useful, especially when the intestinal flora is deficient or unbalanced, as a result of incorrect diet, of drugs (especially antibiotics), of climatic stresses, of digestive disorders or deficiencies. In fact, these conditions cause diarrhea, constipation, flatulence, maldigestion, asthenia and malaise due to the toxins produced by the predominance of the putrefactive over the fermenting flora.
- The lactic acid bacteria produce proteases and lipases that complete the digestion of proteins and fats and subtract also these nutrients from the micro-organisms of the intestinal flora that produce toxic substances, e.g. those derived from the anaerobic processes of putrefaction.
- The lactic acid bacteria produce vitamin K, a factor that is necessary for blood clotting, and also several vitamins of group B, required for the energetic metabolism.
- They eliminate intestinal dysmicrobisms, also because they produce special antibacterial substances, the bacteriocins, which impede the growth of the "bad" flora.
- Moreover, the lactic acid bacteria grow and multiply on the intestinal wall, forming a barrier against pathogenic micro-organisms, such as *Candida albicans, Salmonellae, Escherichiae, Staphylococci, Clostridia*, etc., which produce toxins and can cause intestinal infections.
- Finally, the lactic acid bacteria stimulate the immune defences of the gastrointestinal tract, helping to defend our body against infections and toxic allergens.

For the purposes of the invention, lactic acid bacteria consisting of *Lactobacillus* sporogenes (*Bacillus coagulans*), hereinafter abbreviated as Ls, is particularly preferred, because the spores of Ls are stable in normal environmental conditions, do not need storage in refrigerator and remain viable in the gastric and biliary secretions that kill most of the other lactic acid bacteria.

The Ls, in particular, produces by a homofermentative process L-lactic acid, i.e. the isomer that enters in our metabolic pathways and is recommended by the World Health Organization because it does not create a systemic acidosis.

For the production of lactic acid, Ls utilizes the undigested fragments of sugars, subtracting these substrates from other harmful species of the intestinal flora, thus hindering their growth and contributing furthermore to the general well being.

For all these reasons, the lactic acid bacteria and in particular the Ls, are very beneficial probiotic agents that, in addition to enhancing the bioavailability of the SIs, provide several benefits for the general well-being.

A further strengthening of bone health can be achieved adding other beneficial principles for bones and joints. One of this is Horsetail (*Equisetum arvense*) that supplies organic salts of monosilicic acid, soluble entities of silicon easily absorbed in the gastrointestinal tract and therefore easily bioavailable. Silicon, together with phosphorus, fluoride, magnesium and boron, is involved in the processes of deposition of the crystals of hydroxyapatite on the collagen fibrils, i.e. on the organic structures on which the mineral component of the bones is built up. Horsetail contains also equisetonin, a substance with mild diuretic action, useful for correcting water retention often occurring during menopause and causing swelling of the lower limbs and an increase of body weight. It is as well advisable to supplement calcium (together with Vitamin D to favour its absorption and deposition in bone) because in menopause there is always an increased demand for calcium.

Experimental

The goal of the experimental part was to investigate the role of the different ingredients in the prevention of bone loss in ovariectomized rats, a well-known model of post-menopausal osteoporosis [6].

Briefly, 95 days old Sprague-Dawley rats were ovariectomized under equitesin anaesthesia 3 ml/kg body weight intraperitoneal (equitesin is a mixture of pentobarbital, ethanol, chloral hydrate, propylene glycol, magnesium sulphate dissolved in water). The animals were divided into 4 groups of 8 animals each. A 5$^{th}$ group of 8 animals was sham operated and kept as non-ovariectomized controls. The rats had free access to water and were fed ad libitum with Harlan diet for rodents enriched with calcium carbonate (0.1 g/kg diet) and cholecalciferol (1 μg/kg diet). SIs and Ls were suspended in 0.5% hy-droxy-propyl-methyl-cellulose in water, hereinafter called VEHICLE, and daily administered with gastric tube in a dose of 10 ml/kg body weight.

The groups were treated as follows.

Group 1. Sham operated, non-ovariectomized controls: VEHICLE

Group 2. Ovariectomized conrols: VEHICLE

Group 3. Ovariectomized treated with SIs: genistin 0.5 mg/kg body weight+daidzin 0.5 mg/kg body weight Group 4. Ovariectoinized treated with SIs+Ls: genistin 0.5 mg/kg body weight+daidzin 0.5 mg/kg body weight+8 million per kg body weight spores of Ls Group 5. Ovariectoimzed treated with SIs+Ls+*Equisetum*: genistin 0.5 mg/kg body weight+daidzin 0.5 mg/kg body weight+8 million per kg body weight spores of Ls+1.5 mg/kg body weight Horsetail shoots dry extract (standardized in 7% silicon dioxide).

The doses were based on those generally recommended for human use, adapting them to the body weight of the rats used in the study.

Soy isoflavones: the usual daily doses are 20–80 mg, preferably 40–60 mg.

*Lactobacillus* sporogenes: the usual daily doses are 75–750 million spores, preferably 250–500 million.

Horsetail: the usual daily doses are equivalent to 3–10 mg silicon dioxide.

Calcium: The Recommended Daily Dietary Allowance (RDDA) in adult women is 800 mg. For the purposes of the invention, a daily dose from 100 to 300 mg is preferred, as supplement to the calcium contained in the normal diet.

Vitamin $D_3$: The RDDA in adult women is 5 μg. For the purposes of the compositions of the invention, a daily dose from 3 to 5 μg is preferred.

Six weeks after ovariectomy, the rats were killed by cervical dislocation under ether anesthesia. The uteri were extracted an immediately weighed, the femurs were freed from the soft tissues, their length was measured with a calliper, volume and density were measured by Archimedes' principle, then they were ashed for 24 h at 640° C. Each ash sample was weighed and dissolved in 6 N HCl. Calcium was measured in the resulting solution by atomic absorption spectrophotometry and phosphorus by calorimetric analysis.

The averages and standard errors of the different results were calculated and the significance between values estimated by Student's t-test.

The results obtained at the end of the study are reported in Table 1 and can be summarized as follows.

1. Six weeks after ovariectomy there was no significant change of body weight in any of the ovariectomized animal groups vs. sham operated animals (Group 1).

2. Conversely, in the ovariectomized controls (Group 2) there was a very significant decrease of the weight of uterus and a significant decrease in the length, density, ash weight, calcium and phosphorus content of the femurs, showing the negative effects of the estrogen deficiency on bone trophism.

3. The administration of SIs (Group 3) had no significant effects (vs. Group 2) on body weight and on uterus (absence of stimulation of alpha estrogen receptors), but increased significantly the femoral length and the bone phosphorus, showing a moderate positive effect on bone trophism.

4. The addition of Ls to SIs (Group 4) notably and surprisingly improved bone trophism, as shown by the significant increase of all bone trophism markers (femur length, density, ash weight, calcium and phosphorus content), supporting the rationale of the SIs–Ls combination to enhance the positive effects of the SIs on bone by favouring the bioavailability of the SIs.

5. The further addition of Horsetail extract (Group 5) elicited a further unexpected improvement in all bone trophism markers (femur length, density, ash weight, calcium and phosphorus content), confirming the anabolic effects of this natural herbal product on the bone.

In conclusion, Ls remarkably strengthens the anabolic effects of SIs on the bone, due to the enhancement of the bioavailability of SIs and to the enhancement of intestinal calcium and phosphorus absorption elicited by the probiotic properties of Ls. The addition of Horsetail extract promotes a further beneficial effect on bone anabolism. Notably, neither SIs nor SIs+Ls, had significant effects on the weight of uterus, showing the absence of the stimulation of the alpha estrogen receptors. This is an important contrast with the effects elicited by estrogen hormones, which enhance bone trophism but may cause in some patients unwanted effects, especially by prolonged use, due to the stimulation of the alpha estrogen receptors by these agents.

The study supports therefore the rationale of the SIs+Ls combination as a natural and well tolerated treatment to prevent bone loss due to the deficiency of estrogen hormones caused by ovariectomy in the rat, which occurs also in women after menopause. The addition of Horsetail extract reinforces the prevention of bone loss elicited by the SIs+Ls combination.

Table 1. Results Found in the Different Groups after 6 Weeks of Treatment. Averages and Standard Errors N of body weight and uterus=8; N of femur data=16. Percent changes vs. ovariectomized controls of Group 2 are also reported. The significant changes ($P_t$<0.05) are in italics.

| | Group | | | | |
|---|---|---|---|---|---|
| | 1 Sham control | 2 Ovx control | 3 SIs | 4 SIs + Ls | 5 SIs + Ls + Equ |
| Body weight g | 262 ± 6 | 260 ± 5[a] | 264 ± 7[b] +2% | 266 ± 6[b] +2% | 263 ± 8[b] +1% |
| Uterus mg | 186 ± 11 | 50 ± 4[c] | 48 ± 6[b] −4% | 57 ± 5[b] +14% | 53 ± 4[b] +6% |
| Femur | | | | | |
| Length mm | 34.2 ± 0.2 | 33.3 ± 0.2[d] | 34.8 ± 0.3[e] +4.5% | 35.0 ± 0.2[e] +5% | 35.4 ± 0.3[e] +6% |
| Density g/cm$^3$ | 1045 ± 13 | 958 ± 12[c] | 965 ± 11[b] +1% | 988 ± 9[f] +3% | 999 ± 10[g] +4% |
| Ash weight g/cm$^3$ | 665 ± 0.07 | 579 ± 6[c] | 595 ± 7[b] +3% | 605 ± 9[g] +4% | 615 ± 7[e] +6% |
| Calcium mmole/cm$^3$ | 7.02 ± 0.1 | 6.35 ± 0.06[c] | 6.54 ± 0.10[b] +3% | 6.75 ± 0.11[e] +6% | 6.88 ± 0.14[e] +8% |
| Phosphorus mmole/cm$^3$ | 3.80 ± 0.03 | 3.46 ± 0.02[c] | 3.55 ± 0.03[g] +3% | 3.66 ± 0.03[e] +6% | 3.70 ± 0.03[e] +7% |

[a]$P_t$ NS vs. Group 1
[b]$P_t$ NS vs. Group 2
[c]$P_t$ < 0.001 vs. Group 1
[d]$P_t$ < 0.05 vs. Group 1
[e]$P_t$ < 0.001 vs. Group 2
[f]$P_t$ = 0.05 Group 2
[g]$P_t$ < 0.05 vs. Group 2

DETAILED DESCRIPTION OF THE INVENTION

The following are examples that describe possible practical application of the present invention but do not limit the invention to the examples.

EXAMPLE 1

Tablets for Oral Use

The following formulation regards the active ingredients and the excipients (with their technical functions) that can be used to formulate tablets for oral administration under the present invention.

The daily dose is contained in a single tablet. The tablets are prepared according to the current technical knowledge and without the need of any particular or special procedure. In summary the following production steps are requested:

- weighing of the individual ingredients;
- preparation of the tableting mix by blending the formulation ingredients in a suitable dry powders mixer;
- compression of the resulting mix in a suitable automatic tableting machine to obtain tablets having the required shape and size.

The needed ingredients are listed in the following Tables.

| Active ingredients | Quantity/Tablet |
|---|---|
| Calcium carbonate (*) | 335 mg |
| Corresponding to Calcium | 121 mg |
| Vitamin $D_3$ 500,000 IU/g | 0.4 mg |
| Corresponding to Vitamin $D_3$ | 5 µg |
| Soy Isoflavones 40% dry extract | 150 mg |
| Corresponding to Isoflavones | 60 mg |
| Equisetum arvense 7% dry extract | 100 mg |
| Corresponding to $SiO_2$ | 7 mg |
| *Lactobacillus sporogenes* 15 billion/g | 34 mg |
| Corresponding to spores | 500 million |
| Dicalcium phosphate dihydrate (**) | 87 mg |
| Corresponding to Calcium | 20 mg |

(*) Contains 36% m/m Calcium
(**) Used also as excipient

| Excipients | Quantity/Tablet | Function |
|---|---|---|
| Calcium dibasic phosphate dihydrate | 87.0 mg | Glidant/Anticaking |
| Hydroxypropylcellulose | 40.0 mg | Binder |
| Microcrystalline cellulose | 16.6 mg | Diluent/Disintegrant |
| Talc | 16.0 mg | Glidant |
| Silicon dioxide | 7.0 mg | Adsorbent/Anticaking |
| Magnesium stearate | 14.0 mg | Lubricant |

EXAMPLE 2

Capsules for Oral Use

The following formulation regards the active ingredients and the excipients (with their technical functions) that can be used to prepare capsules for oral administration under the present invention.

The daily dose is carried in two capsules. The capsules are prepared according to the current technical knowledge and without the need of any particular or special procedure. In summary the following production steps are requested:

- weighing of the individual ingredients;
- preparation of the formulation for capsules filling in a blender suitable for the dry mixing operation;
- hard gelatine capsules of the due size and desired colour, filling carried out in an automatic encapsulation machine.

The needed ingredients are listed in the following Tables.

| Active ingredients | Quantity/ Capsule |
|---|---|
| Calcium carbonate (*) | 176.2 mg |
| Corresponding to Calcium | 60.5 mg |
| Vitamin $D_3$ 500,000 IU/g | 0.2 mg |
| Corresponding to Vitamin $D_3$ | 2.5 µg |
| Soy Isoflavones 40% dry extract | 75 mg |
| Corresponding to Isoflavones | 30 mg |
| *Equisetum arvense* 7% dry extract | 50 mg |
| Corresponding to $SiO_2$ | 3.5 mg |
| *Lactobacillus sporogenes* 15 billion/g | 17 mg |
| Corresponding to spores | 250 million |

(*) Contains 36% m/m Calcium

| Excipients | Quantity/Capsule | Function |
|---|---|---|
| Starch | 60.0 mg | Diluent/ Disintegrant |
| Microcrystalline cellulose | 29.0 mg | Diluent |
| Magnesium stearate | 5.0 mg | Lubricant |
| Talc | 2.6 mg | Glidant |

EXAMPLE 3

Sachets Containing Powder for Extemporaneous Oral Suspension

The following formulation regards the active ingredients and the excipients (with their technical functions) that can be used to formulate a powder suitable to prepare an oral suspension.

The daily dose is carried in a single portion of powder. The portions are contained in sachets consisting of an external paper layer, an aluminium interface and an internal polyethylene layer. The sachets are prepared according to the current technical knowledge and without the need of any particular or special procedure. In summary the following production steps are requested:

weighing of the individual ingredients;

homogenisation of the ingredients in a blender suitable for the dry mixing operations;

thermoforming of the sachets in a suitable automatic line including filling and sealing thereof as well;

filling and sealing of the sachets on the above described automatic line to obtain sachets of the desired size and shape, containing the monodose powder for extemporaneous use.

The needed ingredients are listed in the following Tables.

| Active ingredients | Quantity/ Sachet |
|---|---|
| Calcium carbonate (*) | 335 mg |
| Corresponding to Calcium | 121 mg |
| Vitamin $D_3$ 500,000 IU/g | 0.4 mg |
| Corresponding to Vitamin $D_3$ | 5 µg |
| Soy Isoflavones 40% dry extract | 150 mg |
| Corresponding to Isoflavones | 60 mg |
| *Equisetum arvense* 7% dry extract | 100 mg |
| Corresponding to $SiO_2$ | 7 mg |
| *Lactobacillus sporogenes* 15 billion/g | 34 mg |
| Corresponding to spores | 500 million |

(*) Contains 36% m/m Calcium

| Excipients | Quantity/Sachet | Function |
|---|---|---|
| Sorbitol | 60.0 mg | Diluent/Sweetener |
| Citric acid | 25.0 mg | Taste enhancer |
| Polyethylenglycole 4000 | 10 mg | Lubricant/Plasticizer |
| Others (*) | q.s. | Sweetener and flavouring agents |

(*) Sweetener and flavouring agents may be freely added, depending on the preferences

REFERENCES

[1] Ho S C. Body measurements, bone mass and fractures-does the East differ from the West? Clin Orthp Rel Res 1996; 323:75–80

[2] Alekel D L, Germain A S, Peterson C T, Hanson K B, Stewart J W, Toda T. Isoflavone-rich soy protein isolate attenuates bone loss in the lumbar spine of perimenopausal women. Am J Clin Nutr 2000; 72:844–852

[3] Mei J, Yeung S S, Kung A W. High dietary phytoestrogen intake is associated with higher bone mineral density in postmenopausal but not premenopausal women. J Clin Endocrinol Metab 2001; 86:5217–5221

[4] Potter S M, Baum J A, Teng H, Stillman R J, Shay N F, Erdman J W Jr. Soy protein and isoflavones: their effects on blood lipids and bone density in postmenopausal women. Am J Clin Nutr 1998; 68(suppl):1375S–1379S

[5] Scheiber M D, Liu J H, Subbiah M T, Rebar R W, Setchell K D. Dietary inclusion of whole soy foods results in significant reductions in clinical risk factors for osteoporosis and cardiovascular disease in normal postmenopausal women. Menopause 2001; 8:384–392

[6] Draper C R, Edel M J, Dick I M, Randall A G, Martin G B, Prince R L. Phytoestrogens reduce bone loss and bone resorption in ophorectomized rats. J Nutr 1997; 127:1795–1799

[7] Izumi T, Pistula M K, Osawa S, Obata A, Tobe K, Saito M, Kataoka S, Kubota Y, Kikuchi M. Soy Isoflavones Aglycones are adsorbed faster and in higher amounts than their glucosides in humans. J Nutr 2000; 130: 1695–1699

[8] Boriello S P, Setchell K D R, Axelson M, Lawson A M. Production and metabolism of lignans by the human faecal flora. J Appl Bacteriol 1985; 58:37–43

[9] Setchell K D R, Boriello S P, Hulme P, Kirk D N, Axelson M. Non-steroidal estrogens of dietary origin: possible roles in hormone-dependent diseases. Am J Clin Nutr 1984; 40:569–578.

What is claimed is:

1. A composition for treating climacteric and menopausal disorders affecting women in pre-, peri-, and post-menopause comprising effective amounts of soy isoflavones and viable lactic acid bacteria comprising at least *Lactobacillus* sporogenes (*Bacillus coagulans*), and further comprising

*Equisetum arvense* dry extract, wherein the composition is provided in pharmaceutical dosage forms for oral administration.

2. A composition according to claim 1, wherein said lactic acid bacteria consist of *Lactobacillus* sporogenes (*Bacillus coagulans*).

3. A composition according to claim 1, wherein said dosage form for administering soy isoflavones is a daily dose of from 20 to 80 mg.

4. A composition according to claims 1 or 2, wherein said dosage form for administering said lactic acid bacteria in a daily dose is from 75 to 750 millions spores.

5. A composition according to claim 1, wherein said dosage form for administering *Equisetum arvense* dry extract is a daily dose from 3.0 to 10.0 mg expressed as silicon dioxide contained in said dry extract.

6. A composition according to claim 1, further containing a pharmaceutically acceptable calcium salt and/or Vitamin $D_3$.

7. A composition according to claim 1, wherein said dosage form is selected from the group consisting of tablets, capsules or sachets containing powder for extemporaneous suspension.

8. A composition according to claim 1, wherein said dosage for administering soy isoflavones in a daily dose is from 40 to 60 mg.

9. A composition according to claims 1 or 2, wherein said dosage form for administering said lactic acid bacteria in a daily dose is from 250 to 500 millions spores.

10. A composition according to claim 1, wherein said dosage form for administering *Equisetum arvense* dry extract in a daily dose is from 5 to 7 mg expressed as silicon dioxide contained in said dry extract.

11. A method for treatment of climacteric and menopausal disorders affecting women in pre-, peri- and post-menopause, comprising orally administering an effective amount of a composition comprising soy isoflavones and viable lactic acid bacteria comprising at least *Lactobacillus* sporogenes (*Bacillus coagulans*), wherein the composition is provided in pharmaceutical dosage forms for oral administration.

12. A method for the treatment according to claim 11, for the treatment of the bone loss that may follow menopause or other forms of ovarian insufficiency.

13. A method for treatment of climacteric and menopausal disorders affecting women in pre-, peri- and post-menopause according to claim 11, wherein the lactic acid bacteria consists of *Lactobacillus* sporogenes (*Bacillus coagulans*).

14. A method for treatment of climacteric and menopausal disorders affecting women in pre-, peri- and post-menopause according to claim 11 or 13, the composition further comprising *Equisetum arvense* dry extract.

15. A method for treatment of climacteric and menopausal disorders affecting women in pre-, peri- and post-menopause according to claim 11 or 13, wherein the composition is in tablet form.

16. A method for treatment of climactenic and menopausal disorders affecting women in pre-, peri- and post-menopause according to claim 14, wherein the composition is in tablet form.

* * * * *